United States Patent [19]

Halfpenny

[11] Patent Number: 4,705,033
[45] Date of Patent: Nov. 10, 1987

[54] HUMIDIFICATION FACE MASK

[75] Inventor: Paul F. Halfpenny, Van Nuys, Calif.

[73] Assignee: Lockheed Corporation, Calabasas, Calif.

[21] Appl. No.: 632,370

[22] Filed: Jul. 19, 1984

[51] Int. Cl.[4] .......................................... A61M 15/00
[52] U.S. Cl. ........................... 128/201.13; 128/204.13; 128/203.26
[58] Field of Search ...................... 128/204.13, 203.29, 128/201.13, 203.22, 207.12, 203.26

[56] References Cited

U.S. PATENT DOCUMENTS

| | | | |
|---|---|---|---|
| 217,691 | 7/1879 | Hurd | 128/204.13 |
| 2,228,502 | 1/1941 | Boothby | 128/201.13 |
| 3,642,201 | 2/1972 | Potchen | 236/44 |
| 3,881,482 | 5/1975 | Lindholm | 128/201.13 |
| 3,980,080 | 9/1976 | Muto | 128/146 |
| 4,146,026 | 3/1979 | Montalvo | 128/146 |
| 4,267,831 | 5/1981 | Aquilar | 128/203.22 |
| 4,272,014 | 6/1981 | Halfpenny et al. | 236/44 B |
| 4,304,230 | 12/1981 | Seufert | 128/206 |

FOREIGN PATENT DOCUMENTS 322790 12/1929 United Kingdom ........... 128/201.13

Primary Examiner—Henry J. Recla
Attorney, Agent, or Firm—Louis L. Dachs

[57] ABSTRACT

The invention is a humidification face mask 10 comprising a closed container 12 having side walls 20 and first and second end walls 14 and 16. The first wall 14 incorporates an aperture 30 therethrough. A flexible, tubular-shaped member 60 is provided, having first and second ends 61 and 62. The first end 61 is coupled to the second end wall 16 and the opposite end 62 is adapted to fit over the mouth and nose. An inlet valve 36 is provided which is adapted to allow humidified air from the interior of the container 12 to the interior of the member 60. A vent valve 33, biased to the closed position, is provided which is adapted to allow exhausted air in the member 60 to pass into the interior of the container 12. A passage assembly 40 coupling the vent valve 33 to the interior of the container 12 is also provided. An open-celled foam member 42 is mounted within the container 12 between the aperture 30 and the inlet valve 36 adapted to receive and hold water. The passage assembly 40 passes through the foam member 42 which completely separates the inlet valve 36 from the aperture 30. The side wall 20 is releasably engageable from the second end wall 16 with a detent assembly 22, 24 adapted to releasably secure the side wall 20 to said second end wall 16. Additionally, an alignment assembly 52 is provided so that the side wall 20 is secured to the second end wall 16 with the vent valve 33 aligned with the passage assembly 40.

7 Claims, 3 Drawing Figures

HUMIDIFICATION FACE MASK

TECHNICAL FIELD

The invention relates to prtective masks and, in particular, to a mask adapted to humidify air for a passenger aboard an aircraft.

BACKGROUND ART

Controlling the relative humidity level in an aircraft is desirable in order to maintain a comfortable environment for the people within. If the relative humidity in an aircraft is too low, generally below 10%, passengers become uncomfortable due to the occurrence in a long-duration flight of, for example, dry, itchy skin, nasal irritation, and gritty eyes. This condition of low relative humidity naturally occurs in modern, jet-powered, commercial aircraft which typically use bleed air from the engines and/or the auxiliary power unit (APU) as the source of air for pressurization. The bleed air from the various compressor stages of the engines are interconnected by bleed-air ducts and control valves and fed to as many as three separate air-conditioning systems. The air exiting the air-conditioning systems is mixed in a plenum chamber and distributed to the passage compartment by ducting mounted above the passenger compartment. The air circulates through the passenger compartment, down through the below-deck cargo compartment walls, and then out flow-control valves mounted in the bottom of the fuselage. The use of such a system at altitudes above 25,000 ft., however, reduces the relative humidity in the passenger compartment to a value of about 5-7% causing the uncomfortable conditions mentioned above. In the past, only centrally located humidification systems were used in aircraft.

In a centrally located humidification system, moisture must be introduced into the above-mentioned air-conditioning systems. While a 50% relative humidity level is considered to be ideal for passenger comfort, levels of 15-30%, still adequate to ensure passenger comfort even on flights as long as 9 to 11 hours, are desirable to reduce the amount of water that must be carried on board the aircraft to raise the humidity, as such additional water adds weight, and therefore, increases fuel consumption and reduces payload. Additionally, maintaining the relative humidity at below 30% reduces the possibility of condensation of moisture on cold surfaces, thereby reducing the possibility of corrosion to the aircraft structure. It also reduces the condensation of moisture on the overhead structure of the passenger compartment, thus, reducing the possibility of water droplets forming which can fall on the passengers and crew.

Typical prior art centrally located humidification systems designed for use in aircraft are either closed-loop systems such as disclosed in U.S. Pat. No. 3,642,201, "Humidifier Control", by P. E. Potchen, or an open-looped system such as disclosed in U.S. Pat. No. 4,272,014, "Humidification System" by P. F. Halfpenny, et al., both of which function well but add considerable weight to the aircraft and are expensive to install and maintain. Thus, most aircraft do not incorporate such systems. It would, therefore, be desirable to eliminate the need for such systems.

While no individual system such as a humidification face mask was discovered in our review of the prior art, several patents used water as a contaminant filter in a face mask; they are U.S. Pat. No. 3,980,080, "Air Filtration Gas Mass" by R. Muto, U.S. Pat. No. 4,146,026, "Filter Mask" by V. H. Montalvo, and U.S. Pat. No. 4,304,230, "Liquid Barrier Filter and Method of Operation" by W. D. Seufert. However, in hospitals, oxygen supplied to patients is, typically, passed through a container of water to humidify the oxygen prior to inhaling by the patient.

Accordingly, it is a general object of the present invention to provide a humidification face mask for passengers on board an aircraft that eliminates the need for a central humidification system.

It is another object of the present invention to provide a humidification face mask that is inexpensive to manufacture.

It is a further object of the present invention to provide a humidification face mask that can easily be replenished with water so as to be continually usable on an extended flight.

DISCLOSURE OF INVENTION

The invention is a humidification face mask comprising a closed container having side walls and first and second end walls. The first wall incorporates an aperture therethrough. A flexible, hollow conical-shaped member is provided, having first and second ends. The first end is coupled to the second end wall and the second end is adapted to fit over the mouth and nose.

An inlet valve means is provided which is adapted to allow humidification air from the interior of the container to the interior of the conical member. A vent valve means biased to the closed position is provided which is adapted to allow exhausted air in the conical member to pass into the interior of the container. A passage means connecting the vent valve to the exterior of the container is also provided.

An open-celled foam member, adapted to receive and hold water, is mounted within the container between the aperture and the inlet valve. Preferably, the passage means passes through the foam member and the foam member completely separates the inlet valve means from the aperture.

The side wall is releasably engageable from the second end wall by means of a detent means. Additionally, alignment means are provided so that when the side wall is secured to the second end wall, the vent valve will be aligned with the passage means.

In a simplified version, the inlet and vent valves and the passage means are eliminated and the exhaled and inhaled air pass directly through the wetted foam member.

The novel features which are believed to be characteristic of the invention, both as to its organization and method of operation, together with further objects and advantages thereof, will be better understood from the following description connected with the accompanying drawings in which presently preferred embodiments of the invention are illustrated by way of examples. It is to be expressly understood, however, that the drawings are for purposes of illustration and description only and are not intended as a definition of the limits of the invention.

BRIEF DESCRIPTION OF DRAWINGS

Illustrated in FIG. 1 is a perspective view of the humidification face mask.

Illustrated in FIG. 2 is a cross-sectional view of the humidification face mask as shown in FIG. 1 along the line 2—2.

Figures 2, 3:
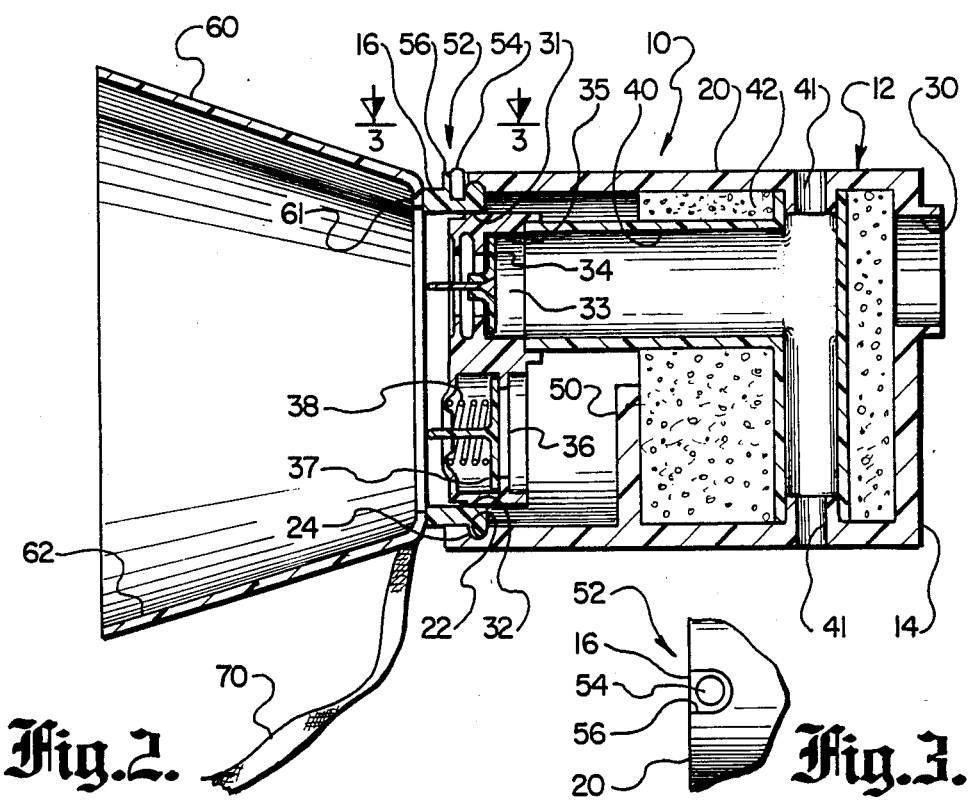

Illustrated in FIG. 3 is a partial view of the humidification face mask shown in FIG. 2 substantially along the line 3—3.

BEST MODE FOR CARRYING OUT THE INVENTION

Figure 1:
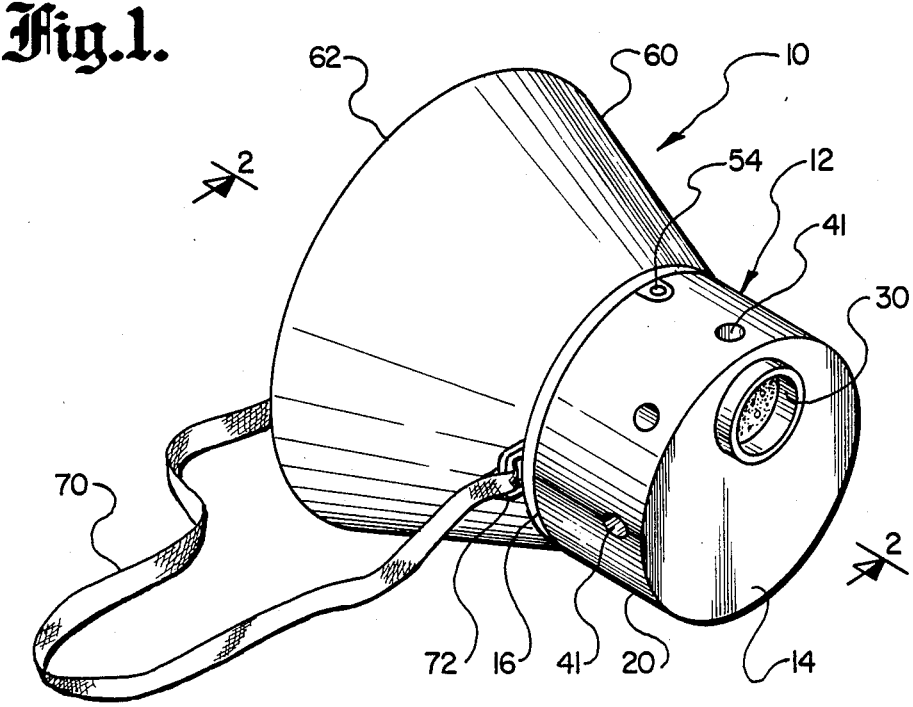

Referring initially to FIGS. 1 and 2, it can be seen that the humidification face mask, generally designated by numeral 10, comprises a container 12. The container 12 includes first and second end walls 14 and 16 and a side wall 20. The container is, generally, tubular in shape. The side wall 20 is, preferably, releasably engageable with the second end wall 16. This is accomplished by providing a groove 22 on the side wall 20 and protrusion 24 on the periphery of the second end wall 16. Preferably, the container is made of a semi-flexible material. An aperture 30 is incorporated in the first end wall 14 and apertures 31 and 32 are incorporated in the second wall 16.

Mounted within aperture 31 is a vent valve 33. The vent valve 33 is essentially a check valve which includes a flexible sealing diaphragm 34 mounted in a hollow housing 35. Mounted in aperture 32 is an inlet valve 36 which is preferably a poppet-type check valve, with the poppet 37 biased by the spring 38 to the closed position. Both the vent valve 33 and inlet valve 36 are well-known designs typically used in aircraft oxygen masks. The apertures 30 and 31, 32 in the first and second walls, respectively, are positioned so as to prevent any liquid water which may collect in excess of the holding capacity of the foam member from leaking out of the container. The apertures are also located and sized to provide a uniform flow through the foam member to increase both heat and mass transfer from the inhaled and exhaled air to the liquid water and foam member. A passenger means 40 couples the vent valve 33 to the exterior of the container 12 via holes 41 in the side wall 20.

Mounted within the container 12 is a open-celled foam member 42 in which a portion of the passage means 40, preferably, passes through. The advantage of using open-celled foam is that the water will be drawn into the foam member because of capillary attraction and will be spread somewhat uniformly throughout, producing a large surface area and ensuring that sufficient moisture is picked up as the passenger breathes. A partial wall 50 is mounted within the container 12 in order to position and retain the foam member 42.

The passage means 40 must be alignd with the vent valve 33 and, since the side wall 20 is releasably engageable with the second wall 16, an alignment means 52, best illustrated in FIGS. 2 and 3, is provided. The alignment means 52 includes a pin 54 partially imbedded in the second wall 16 and the side wall 20 having a notch 56 engagable therewith. Thus, the side wall 20 can only be releaseably engaged with the second end wall 16 when the notch 56 is aligned with the pin 54. Attached to the second side end wall 16 is a flexible conical-shaped member 60 having a first end 61 attached to the second end wall 16 and its opposite end 62 adapted (deformable) to cover the nose and mouth.

An adjustable strap 70 is attached to eyelets 72 (only one of which is shown) mounted on the second end wall 16 which can be used to attach the mask to the person by stretching the strap 70 over the head.

In operation, one need only pour a measured amount of water through the aperture 30, preferably by means of a hermetically sealed vial (not shown). The water will be absorbed by the foam member 42 and will slowly evaporate as the person inhales and exhales. Upon exhaling, the warm expired air will flow through the passage means 40 and will tend to warm the water (via conduction of heat through the walls of the passage means), aiding in the evaporation thereof. Having the vent valve 33 coupled via passage means 40 to the exterior of the container 12 prevents mouth odor from being absorbed by the moisture-laden foam member. On a long flight, should all the water be evaporated, one need only refill the foam member via the aperture 30.

A simplified and less expensive version of the above-described humidification face mask 10 can be fabricated by eliminating the valves 33 and 36 and passage means 40 and making the open-celled foam member "solid" with a number of apertures provided in each end wall. In this variation, exhaled and inhaled air would pass through the foam member. The disadvantage is that breath odor would likely be absorbed by the wetted foam.

While the humidification system has been described with reference to particular embodiments, it should be understood that the embodiments are merely illustrative as there are numerous variations and modifications which may be made by those skilled in the art. Thus, the invention is to be construed as being limited only by the spirit and scope of the appended claims.

INDUSTRIAL APPLICABILITY

The humidification face mask is useful in low-humidity environments, particularly, on jet-powered, commercial aircraft flying at high altitudes, providing increased passenger comfort.

I claim:

1. A humidification face mask comprising:
   a closed container having side walls and first and second end walls, said first end wall having an aperture therethrough;
   a flexible tubular-shaped member having first and second ends, said first end coupled to said second end wall, and said second end adapted to fit over the mouth and nose;
   an inlet valve means biased to the closed position adapted to allow humidified air flow from the interior of said container to the interior of said member;
   vent valve means biased to the closed position adapted to allow exhausted air in said member to flow into said container;
   an open-celled foam member mounted within said container between said aperture and said inlet valve, said foam member adapted to receive and hold water; and
   passage means coupling said vent valve to the exterior of said container, said passage means passing through said foam member.

2. The humidification face mask as set forth in claim 1 wherein said foam member completely separates said inlet valve from said aperture.

3. The humidification face mask as set forth in claim 2 wherein said inlet valve means and said vent valve means are check valves.

4. The humidification face mask as set forth in claim 3 including flexible strap means coupled to said mask such that said strap means can be used to hold said mask to said face.

5. The humidification face mask as set forth in claim 4 wherein said side wall is releasably engageable with said second end wall.

6. The humidification face mask as set forth in claim 5 further including detent means adapted to releasably secure said side wall to said second end wall.

7. The humidification face mask as set forth in claim 6 including alignment means to insure that when said side wall is secured to said second end wall, said vent valve is aligned with said passage means.

* * * * *